United States Patent [19]

Sugi et al.

[11] Patent Number: 5,036,087
[45] Date of Patent: Jul. 30, 1991

[54] CLATHRATE COMPOUND

[75] Inventors: Hideo Sugi; Ayako Sekikawa; Ryoichi Takahashi, all of Tokyo, Japan

[73] Assignee: Kurita Water Industries, Ltd., Tokyo, Japan

[21] Appl. No.: 295,627

[22] Filed: Jan. 10, 1989

[30] Foreign Application Priority Data

Jan. 26, 1988 [JP] Japan .................................. 63-15426

[51] Int. Cl.$^5$ ............................................ A61K 31/41
[52] U.S. Cl. .................................. 514/372; 514/171;
548/213
[58] Field of Search .................... 14/171, 372; 548/213

[56] References Cited

U.S. PATENT DOCUMENTS 4,880,774 11/1989 Joukou ...................................... 512/2
4,973,700 11/1990 Sekikawa ............................. 548/213

FOREIGN PATENT DOCUMENTS 46-21240 6/1971 Japan .
53201 3/1986 Japan ................................. 514/172
22701 1/1987 Japan ................................. 514/172
265226 11/1987 Japan ................................. 514/172

OTHER PUBLICATIONS

Giglio, Inclusion Compounds of Deoxycholic acid, Inclusion Compounds, 1984, 2, 207–229.
Meirovitch, J. Phys. Chem., 89 2389 (1985).

Primary Examiner—Robert Gerstl
Attorney, Agent, or Firm—Kanesaka and Takeuchi

[57] ABSTRACT

A clathrate compound comprising a water-soluble microbicide and at least one of (a) a bisphenol compound represented by formula (I) and (b) deoxycholic acid represented by formula (II):

(a) bisphenol compound

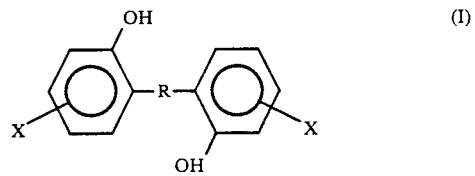

where X is a halogen atom, and R is a methylene, ethylidene, propylidene or isopropylidene group;

(b) deoxycholic acid

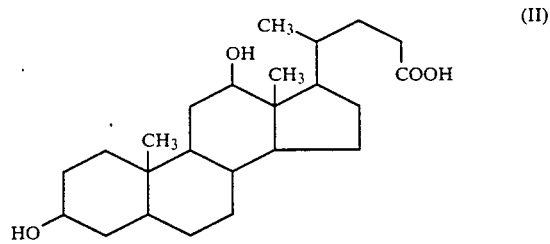

2 Claims, No Drawings

CLATHRATE COMPOUND

FIELD OF THE INVENTION AND RELATED ART STATEMENT

This invention relates to a clathrate compound and a method of producing the same. More particularly, it relates to a novel clathrate compound which is useful as a sustained release antimicrobial agent.

The cooling water systems in various industrial facilities, water systems in paper and pulp making plants, etc. suffer from various kinds of trouble that are caused by the deposition of a slime of animal, vegetable or microbial origin.

In order to prevent such trouble arising from the deposition of slime, it has been customary to use an antimicrobial (or slime control) agent, as it is relatively easy to use and is also inexpensive. While various compounds are known, 5-chloro-2-methyl-4-isothiazoline-3-one (hereinafter referred to simply as "CMI"), which is represented by formula (III) below, is particularly widely used as a slime controller, bactericide, algicide or fungicide in cooling water systems, water systems in the paper and pulp industry, swimming pools and other water systems, because of its high antimicrobial activity:

<chemical structure> (III)

CMI is usually produced by:
(1) the halogenation of β-thioketoamide in an inert organic ester solvent, such as an acetic acid ester; or
(2) the treatment of a β-substituted thiocyanoacrylamide or thiosulfatoacrylamide with an acid to obtain isothiazolone and the halogenation thereof, as disclosed in Japanese Patent Publication No. 21240/1971.

Neither of these two methods (1) and (2) can, however, make a product which is composed solely of CMI. They both can make only a product containing also 2-methyl-4-isothiazoline-3-one (hereinafter referred to simply as "MI"), which is represented by formula (IV) below and has an antimicrobial activity which is as low as only one-tenth of that of CMI:

<chemical structure> (IV)

Moreover, there is not known any method that can separate only CMI from the reaction product. There is no alternative but to use a mixture of CMI and MI having a low degree of antimicrobial activity.

Although CMI has a high degree of antimicrobial activity, its handling requires a great deal of care, as it is highly irritant to the skin. It is difficult to use effectively in water for a long period of time, since it reacts with organic substances in water, such as amines and reducing substances, and thereby loses its antimicrobial activity. No antifouling paint containing CMI can maintain its antifouling effect for a long period of time when used in water, as CMI is easily soluble in water.

The water-soluble antimicrobial agents which have hitherto been commonly used are far from satisfactory, since they are toxic, require a great deal of care when they are handled, lower their antimicrobial activity rapidly and are highly soluble in water.

OBJECTS AND SUMMARY OF THE INVENTION

It is an object of this invention to provide a clathrate compound which can form an excellent sustained release antimicrobial agent overcoming the drawbacks of the known antimicrobial agents as hereinabove pointed out.

It is another object of this invention to provide a clathrate compound which can be used for the preparation of a powdery water-soluble microbicide, and its stabilization, separation and purification.

The clathrate compound of this invention comprises a water-soluble microbicide; and (a) a bisphenol compound of general formula (I) and/or (b) deoxycholic acid, which is represented by formula (II):

(a) bisphenol compound

<chemical structure> (I)

(where X is a halogen atom, and R is a methylene, ethylidene, propylidene or isopropylidene group);

(b) deoxycholic acid

<chemical structure> (I)

The method of this invention is characterized by either mixing a liquid containing (a) a bisphenol compound of formula (I) and/or (b) deoxycholic acid of formula (II) and a water-soluble microbicide, or mixing (a) a bisphenol compound and/or (b) deoxycholic acid in an aqueous solution of a water-soluble microbicide, whereby a solid substance is formed; and separating it from a liquid phase.

According to this invention, CMI, which is represented by formula (III) above, is preferably used as the water-soluble microbicide.

According to this invention, therefore, a watersoluble microbicide, such as CMI, is employed as a guest compound, and a bisphenol compound and/or deoxycholic acid as a host compound, for forming a clathrate compound.

DETAILED DESCRIPTION OF PREFERRED EMBODIMENTS

Referring in detail to this invention, one of the bisphenol compounds which are represented by formula (I) is 2,2'-methylenebis(4-chlorophenol) (hereinafter referred to simply as "MCP"), which is represented by formula (V) below:

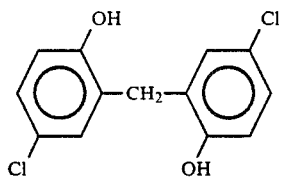

It is possible to use any water-soluble microbicide if it can form a clathrate compound with a bisphenol compound or deoxycholic acid. CMI, which is widely used as an effective microbicide, can be employed for the purpose of this invention, too, though the use of any other microbicide is not precluded.

The clathrate compound of this invention, which comprises a water-soluble microbicide as a guest compound and at least either a bisphenol compound or deoxycholic acid as a host compound, can be produced easily in the presence of a solvent or in the absence of any solvent by the method of this invention.

When a solvent is employed, it is possible to use any ordinary water-soluble solvent such as methanol, ethanol or acetone, or any ordinary water-insoluble solvent or dispersant such as benzene, toluene, xylene or chloroform. A liquid in which a host compound is dissolved or dispersed using any such solvent or dispersant is mixed with a watersoluble microbicide, such as CMI, or a mixture of a watersoluble microbicide and impurities, so that the host compound and the microbicide may react with each other, whereby a solid clathrate compound is precipitated. It is separated from the liquid by a customary method of filtration.

Although the clathrate compound of this invention is easy to produce by employing a solvent as hereinabove described, it is more advantageous not to use any solvent. The use of a solvent is likely to bring about a variety of problems including:
(1) It is necessary to choose an appropriate solvent;
(2) It is relatively difficult to select the proper conditions for the reaction;
(3) Special care is required for the disposal of the waste matter resulting from the separation of the solid compound from the liquid;
(4) It is necessary to employ facilities for protecting the workers and their working environment, particularly when an organic solvent is used; and
(5) It is only at a relatively low rate that the host compound can be recovered in the product.
All of these problems can be overcome if no solvent is employed.

When no solvent is employed, the host compound is added directly into an aqueous solution of the water-soluble microbicide and mixed therewith under stirring. The aqueous solution need not necessarily contain only the microbicide, but may contain impurities, too. The host compound which is employed for the purpose of this invention reacts with the water-soluble microbicide so selectively that it is possible to produce a clathrate compound in which only the desired microbicide is included in the host compound, even if the microbicide solution contains any byproduct or other impurities.

Although it is possible to employ any reaction temperature in the range of 0° C. to 100° C., a preferred range is from, say, 10° C. to 30° C. The reaction may be continued for a period of, say, 0.5 to 24 hours.

A solid (or semi-solid) clathrate compound is usually obtained as a result of the reaction. It is separated from the liquid phase, washed with water, and dried, whereby the intended product can be obtained.

The NMR analysis of the clathrate compound can be employed for ascertaining that only the desired guest compound is included in the host compound. It can also be used to determine the molar ratio of the guest compound in the clathrate compound.

The clathrate compound of this invention is usually a powdery solid and is, therefore, easy to form into tablets or any other shape. Insofar as the guest compound is a water-soluble microbicide, the clathrate compound of this invention is so low in toxicity that its handling does not call for any special care. Moreover, there is no possibility that it may react with any other substance and lower its antimicrobial activity while it is in use.

When the clathrate compound of this invention is placed in water, it releases the water-soluble microbicide into water only gradually or in a sustained way. Therefore, it is a useful sustained release antimicrobial agent which can maintain its antimicrobial activity for a very long time.

The clathrate compound of this invention can be used as a sustained release antimicrobial agent in a variety of ways as will hereunder be listed:
(1) The water to be treated is passed through a column packed with the agent;
(2) A bag or cartridge of a material which is permeable to water, but is not soluble therein, is filled with the agent and is submerged or floated in the water to be treated;
(3) The powdery agent or any product molded therefrom is dispersed in the water to be treated;
(4) A mixture of the agent with a paint or any other resinous coating material is applied to the surfaces of equipment in the water system to be protected;
(5) A mixture of the agent with an oily or aqueous ink, medium, or the like is applied to the surface of an object to be protected by printing; and
(6) The agent is caused by any other appropriate method to adhere to the surface to be protected.

This invention also contributes to the preparation of a powdery, stabilized or concentrated water-soluble antimicrobial agent. Moreover, the clathrate compound of this invention can be employed for the separation or purification of any specific water-soluble microbicide, insofar as it is the product of the highly selective reaction taking place between the specific compounds. It is, for example, possible to obtain CMI of high purity if a clathrate compound is produced by the inclusion in a host compound of only CMI from a mixture of CMI and MI, and CMI is separated from the clathrate compound, which have hitherto been difficult to separate from each other.

The water-soluble microbicide such as CMI, can be separated from the clathrate compound:
(1) if the clathrate compound is immersed in water; or
(2) if it is dissolved in an organic solvent and water is added to its solution to cause only the host compound to settle.

In either event, the microbicide is dissolved in water and recovered in the form of its aqueous solution.

The clathrate compound of this invention, in which the water-soluble microbicide is included in a bisphenol compound and/or deoxycholic acid, is useful for the preparation in powder form, stabilization, concentration, separation or concentration of the water-soluble microbicide. Moreover, it provides, among others, a sustained release antimicrobial agent of very high industrial value containing the water-soluble microbicide as its effective component and having a wide variety of advantages including the following:

(1) It can maintain its antimicrobial activity for a long period of time, as its effective component is dissolved in water only gradually;
(2) As it is a solid, it can be formed into tablets or any other shape and is easy to handle;
(3) It contributes to making an improved working environment of higher safety, as the microbicide is included in less toxic and irritant to the skin; and
(4) Its effective component does not undergo any reaction with other substances that may lower its antimicrobial activity.

The clathrate compound of this invention includes the water-soluble microbicide in its solid state and allows it to be dissolved in water only slowly. The imprisonment of the microbicide makes it less toxic and irritant to the skin. Moreover, it prevents the microbicide from reacting with any other substance and losing its antimicrobial activity. Therefore, the clathrate compound of this invention can be used effectively for a sustained release antimicrobial agent maintaining its antimicrobial activity for a very long time.

The clathrate compound of this invention not only enables the preparation in powder form, stabilization and concentration of a water-soluble microbicide, but also is useful for the separation or purification thereof, as only the effective microbicide forms the clathrate compound with the host compound. The clathrate compound which is formed by employing CMI as the water-soluble microbicide provides a particularly good sustained release antimicrobial agent.

The method of this invention can easily and efficiently produce a clathrate compound having excellent properties as hereinabove described, and also enables the preparation in powder form, stabilization, concentration, separation or purification of a water-soluble microbicide.

The invention will now be described more specifically with reference to a number of examples thereof. It is, however, to be understood that the following description is not intended to limit the scope of this invention, but that variations or modifications may be easily made by anybody of ordinary skill in the art without departing from the scope of this invention which is defined by the appended claims.

EXAMPLE 1

Preparation of a Clathrate Compound from MCP and CMI:

0.2 g of MCP was mixed in 1.5 g of an aqueous solution of a water-soluble microbicide consisting mainly of CMI which had a microbicide content of 10.4% by weight. The mixture was stirred at room temperature for four hours, whereby a semi-solid reaction product was obtained. It was separated from the aqueous phase and dried.

The NMR analysis of the product revealed that it was a clathrate compound containing MCP and CMI in a molar ratio of 1:0.35.

EXAMPLE 2

Preparation of a Clathrate Compound from Deoxycholic Acid and CMI:

A solid reaction product was obtained by repeating Example 1, except that deoxycholic acid was employed instead of MCP. It was collected by filtration, washed with water, and dried.

The NMR analysis of the product revealed that it was a clathrate compound containing deoxycholic acid and CMI in a molar ratio of 1:0.37.

EXAMPLE 3

CMI Dissolution Tests:

One gram of each of the clathrate compounds which had been obtained in Examples 1 and 2 was dispersed in one liter of pure water and the water was stirred at 25° C. Samples were taken from the water at certain intervals of time and the amount of CMI which had been dissolved in the water was determined from each sample. The results are shown in Table 1.

TABLE 1

| Amounts of CMI Dissolved from Clathrate Compounds of Examples 1 and 2 (wt. %) | | | | | | |
|---|---|---|---|---|---|---|
| | Time elapsed (h) | | | | | |
| | 0.25 | 0.5 | 1.0 | 2.0 | 4.0 | 7.0 |
| Example 1 | 11.8 | 17.6 | 21.1 | 35.3 | 47.1 | 54.7 |
| Example 2 | — | 17.5 | 20.8 | 25 | 32 | 43.3 |

It is obvious from the results shown in Table 1 that the clathrate compound of this invention provides a sustained release antimicrobial agent which can maintain its antimicrobial activity for a long period of time.

EXAMPLE 4

Preparation of a Clathrate Compound from a Solution of MCP and CMI:

A solution which had been obtained by dissolving 50 g of MCP in 50 ml of methanol was mixed with 267 g of an aqueous solution of a water-soluble microbicide consisting mainly of CMI which had a microbicide content of 10.4% by weight. The mixture was stirred at room temperature for half an hour, whereby a solid reaction product was obtained. It was separated from the liquid, washed with water, and dried.

The NMR analysis of the product revealed that it was a clathrate compound containing MCP and CMI in a molar ratio of 1:0.85

What is claimed is:

1. A clathrate compound comprising 5-chloro-2-methyl-4-isothiazoline-3-one, and at least one of (a) a bisphenol compound represented by formula (I) and (b) deoxycholic acid represented by formula (II):

(a) bisphenol compound

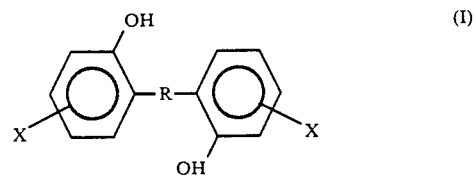

where X is a halogen atom, and R is a methylene, ethylidene, propylidene or isopropylidene group;

(b) deoxycholic acid

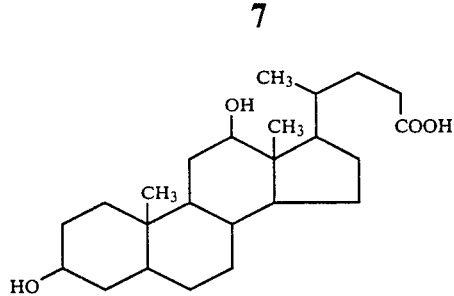
(II)
2. A clathrate compound as set forth in claim 1, wherein said bisphenol compound is 2,2'-methylenebis(4-chlorophenol).
* * * * *